United States Patent [19]
Inoue

[11] Patent Number: 5,997,565
[45] Date of Patent: Dec. 7, 1999

[54] FORCEPS FOR AN ENDOSCOPIC OPERATION

[75] Inventor: Masahide Inoue, Tokyo, Japan

[73] Assignee: Asahi Kogaku Kogyo Kabushiki Kaisha, Tokyo, Japan

[21] Appl. No.: 09/006,435

[22] Filed: Jan. 13, 1998

[30] Foreign Application Priority Data

Jan. 16, 1997 [JP] Japan ..................................... 9-005422
Dec. 10, 1997 [JP] Japan ..................................... 9-339549

[51] Int. Cl.⁶ .................................................. A61B 17/28
[52] U.S. Cl. ........................................................ 606/205
[58] Field of Search .................................... 606/205, 206, 606/207, 208; 81/418, 421; 30/186

[56] References Cited

U.S. PATENT DOCUMENTS

| | | | |
|---|---|---|---|
| 1,359,164 | 11/1920 | Giudice | 606/205 |
| 5,122,130 | 6/1992 | Keller | 606/207 |
| 5,147,357 | 9/1992 | Rose et al. . | |
| 5,152,774 | 10/1992 | Schroeder . | |
| 5,192,298 | 3/1993 | Smith et al. . | |
| 5,368,596 | 11/1994 | Burkhart | 606/207 |
| 5,368,606 | 11/1994 | Marlow et al. | 606/207 |
| 5,649,955 | 7/1997 | Hashimoto et al. . | |
| 5,700,276 | 12/1997 | Benecke | 606/208 |

OTHER PUBLICATIONS

"Development of a lung grasping forceps for VATS," Third Department of Surgery, Toho University School of Medicine, The Society of Thoracoscopic Surgery, 6th Annual Meeting, Tokyo, Japan, Sep. 27–28, 1996.

*Primary Examiner*—Michael Buiz
*Assistant Examiner*—Vikki Trinh
*Attorney, Agent, or Firm*—Greenblum & Bernstein, P.L.C.

[57] ABSTRACT

A forceps includes a pair of grip pieces which are pivotally supported about a first fulcrum to be mutually openable and closable. A pair of tip-end forceps pieces are pivotally supported about a second fulcrum to be mutually openable and closable. The second fulcrum is separated from the first fulcrum. An operation transferring member transfers opening and closing operation of the grip pieces about the first fulcrum to opening and closing operations of the tip-end forceps pieces about the second fulcrum.

8 Claims, 8 Drawing Sheets

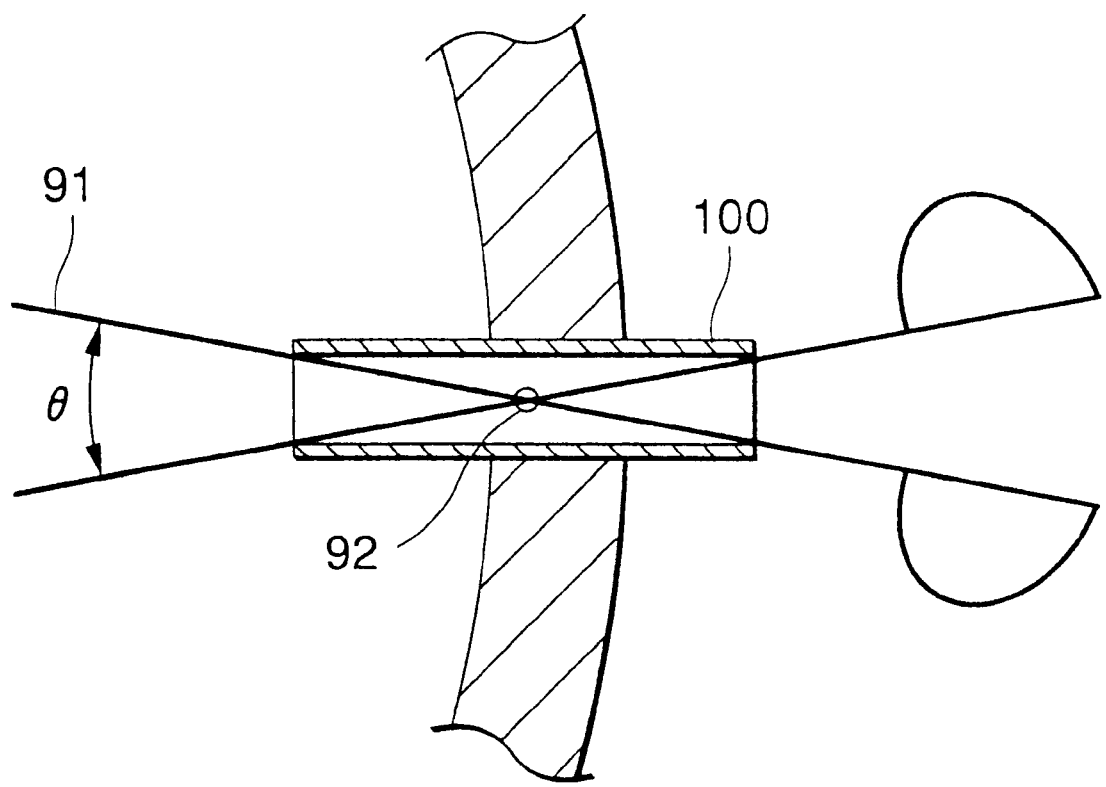

FORCEPS FOR AN ENDOSCOPIC OPERATION

BACKGROUND OF THE INVENTION

1. Field of the Invention

The invention relates to a forceps for an endoscopic operation which is passed through a trocar to be used for performing an endoscopic operation in the body cavity.

2. Description of the Related Art

Recently, in various kinds of operations such as cholecystectomy, an endoscopic operation is widely performed. Such an endoscopic operation is performed without making a large incision and with thrusting plural trocar sheaths (hereinafter, referred to merely as "trocars") which are thin tubular members, into the somatic layer, and passing a surgical instrument and an endoscope through the trocars.

In an endoscopic operation, forceps such as a grasping forceps which grasps organs, and a cutting forceps which cuts organs are necessary. Generally, such forceps are configured so that a pair of members in each of which a grip piece on the side of the basal end and a forceps piece on the side of the tip end are integrally formed are rotatably coupled to each other at a fulcrum in an X-shape.

A forceps is passed through a trocar under a state where forceps pieces at the tip end are closed so as to reduce the size in section. In the body cavity, preferably, the tip end forceps pieces are widely opened.

As shown in FIG. 9, however, the open angle θ of tip end forceps pieces 91 is restricted by the inner diameter of a trocar 100. In a related art forceps for an endoscopic operation which is configured as described above, therefore, the open angle θ is restricted by the both end openings of the trocar 100.

The open angle θ is maximum when the fulcrum 92 is at to the middle of the trocar 100 in the longitudinal direction as shown in FIG. 9, and hence Tan(θ/2) cannot be made large. Unless the trocar 100 is made unrealistically thick and short, consequently, a large open angle θ cannot be attained.

Even when a diseased part is slightly large, therefore, the part cannot be surely grasped or cut. As a result, an endoscopic operation cannot be adequately performed.

SUMMARY OF THE INVENTION

In view of the above problems, an object of the invention is to provide a forceps for an endoscopic operation in which tip end forceps pieces can be widely opened under a state where the forceps is passed through a usual trocar.

In order to attain the object, the forceps for an endoscopic operation of the invention includes: a pair of grip pieces which are pivotally supported to be mutually openable and closable about a first fulcrum; a pair of tip-end forceps pieces which are pivotally supported to be mutually openable and closable about a second fulcrum separated from the first fulcrum; and an operation transferring member which transfers opening and closing operations of the grip pieces about the first fulcrum to opening and closing operations of the tip-end forceps pieces about the second fulcrum.

The operation transferring member preferably has a thickness which passes through a trocar.

The operation transferring member may include an arm which is link-coupled to a first member provided on a first fulcrum side of the grip pieces, and to a second member provided on a second fulcrum side of the tip-end forceps pieces.

The operation transferring member may include: a pin projected from one of a third member provided on a first fulcrum side of the grip pieces, and a fourth member provided on a second fulcrum side of the tip-end forceps pieces; and a long groove which engages with the pin and is formed in the other of the third member and the forth member.

The operation transferring member may include a gear which meshes with a fifth member provided on a first fulcrum side of the grip pieces, and with a sixth member provided on a second fulcrum side of the tip-end forceps pieces.

One of said tip-end forceps pieces may swing across a line connecting the first fulcrum with the second fulcrum, whereby being swingable to the side of the other of the tip-end forceps pieces.

The operation transferring member may have a stopper regulating a swing range of the tip-end forceps pieces.

One of the grip pieces and one of the tip-end forceps pieces may be fixed to each other. The tip-end forceps pieces may be scissors members or grasping members.

The present disclosure relates to the subject matter contained in Japanese patent application No. Hei. 9-005422 filed on Jan. 16, 1997 and Japanese patent application No. Hei. 9-339549 filed on Dec. 10, 1997 which are expressly incorporated herein by reference in theirs entirety.

BRIEF DESCRIPTION OF THE DRAWINGS

FIG. 9 is a diagram showing a use state of a related art forceps for an endoscopic operation.

EXPLANATION OF THE FORCEPS FOR AN ENDOSCOPIC OPERATION

This explanation will be described with reference to the accompanying drawings.

Figure 1:
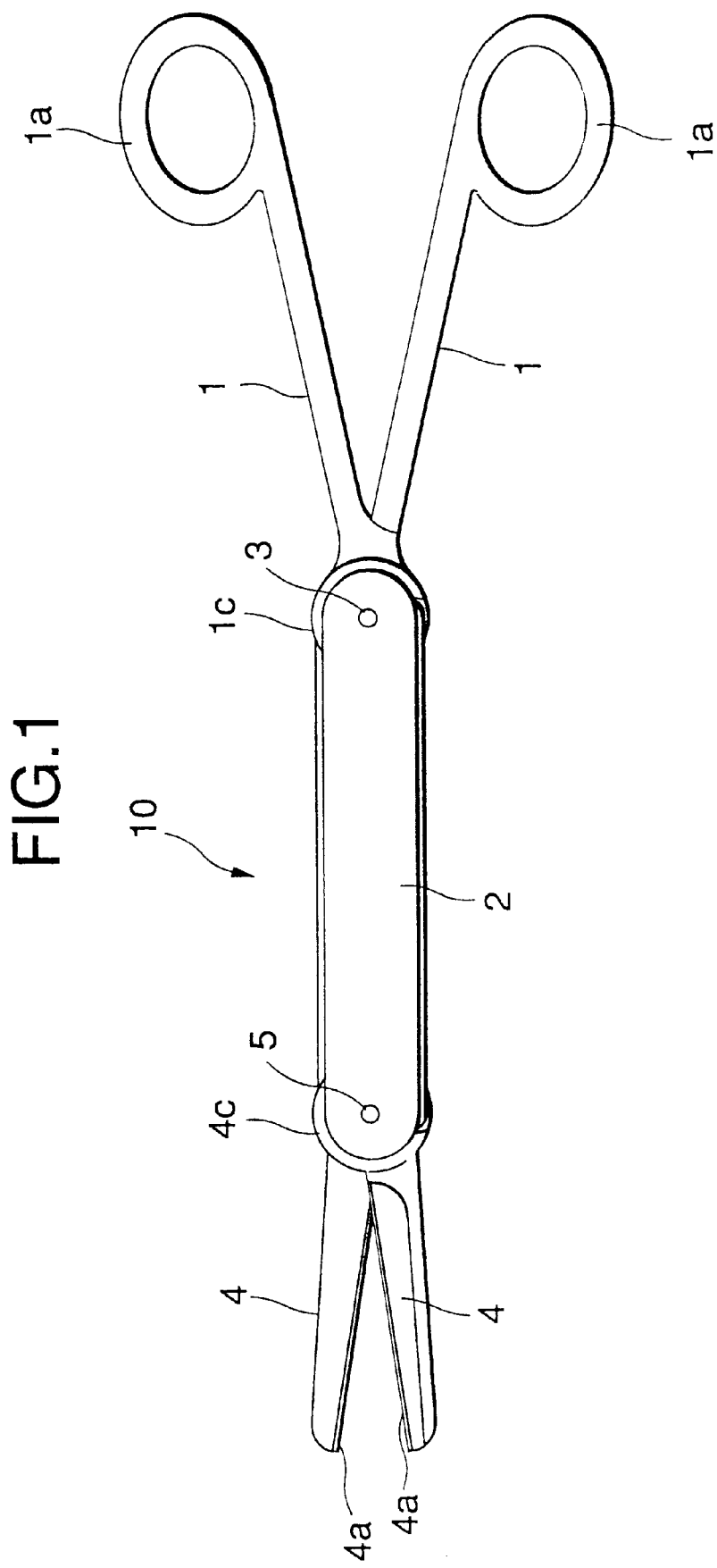
FIG. 1 is a front view of a first cutting forceps for an endoscopic operation.

FIG. 1 shows a cutting forceps which is a first forceps for an endoscopic operation and which is used in an endoscopic operation with being passed through a trocar.

A pair of grip pieces 1 which are disposed on the basal end side are pivotally supported to be mutually openable and closable about a first fulcrum 3 which is disposed in the vicinity of an end of each of support side plates 2. Each of the grip pieces 1 can be independently swung about the first fulcrum 3. A ring-like finger hold 1a is formed in the end portion of each grip piece 1 on the basal end side.

A pair of tip-end forceps pieces 4 on each of which a cutting edge 4a is formed are pivotally supported to be mutually openable and closable about a second fulcrum 5 which is disposed in the other end portions of the support side plates 2 so as to be separated from the first fulcrum 3. The opening and closing operations of the grip pieces 1 are transferred to the tip-end forceps pieces 4, by an operation transferring unit 10 which is disposed along the support side plates 2.

Figure 2:
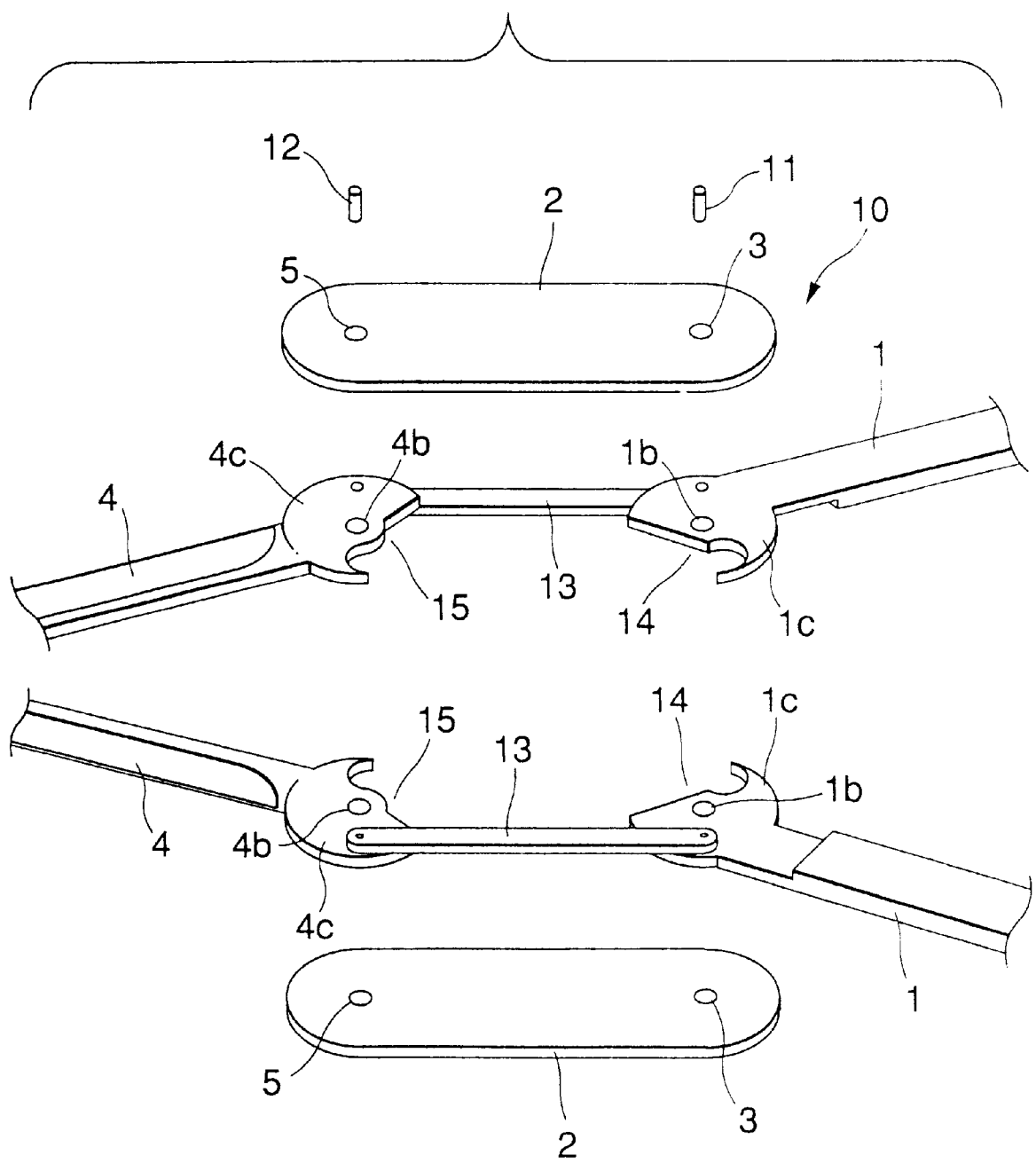
FIG. 2 is an exploded perspective view of an operation transferring unit of the first forceps.

FIG. 2 is an exploded view of the operation transferring unit 10. The paired support side plates 2 are disposed in the outsides on both sides. In each of the support side plates 2, shaft holes are opened at the fulcrums 3 and 5, respectively. Shafts 11 and 12 passing through the shaft holes at the fulcrums 3 and 5 are loosely fitted into shaft holes 1b and 4b which are made in the grip pieces 1 and the tip-end forceps pieces 4, respectively. Therefore, the grip pieces 1 and the tip-end forceps pieces 4 can be swung about the shafts 11 and 12, respectively.

The base portion of each of the grip pieces 1 and the tip-end forceps pieces 4 is formed into a disk-like shape which is centered at the shaft hole 1b or 4b. End portions of rod-like arms 13 which couple the disk portions 1c of the grip pieces 1 with the disk portions 4c of the tip-end forceps pieces 4 are rotatably connected to the disk portions by small pins, respectively.

A pair of arms 13 are disposed so as to respectively couple one of the grip pieces 1 with one of the tip-end forceps pieces 4, and the other grip piece 1 with the other tip-end forceps piece 4. When the grip pieces 1 on the basal end side are operated to be mutually opened or closed, therefore, the operation is transferred to the tip-end forceps pieces 4 via the arms 13, so that the tip-end forceps pieces 4 are mutually opened or closed.

The reference numerals 14 and 15 designate recesses (escapes) which are formed in the disk portions 1c and 4c in order to prevent the disk portions 1c and 4c and the arms 13 from interfering with each other in a required operation range.

The recesses 14, 15 are formed in a shape which regulate the swing range of the tip-end forceps pieces 4 so that the arms 13 are abutted on side surfaces of the recesses 14, 15, when the tip-end forceps pieces 4 are swung about the second fulcrum 5.

Figure 3:
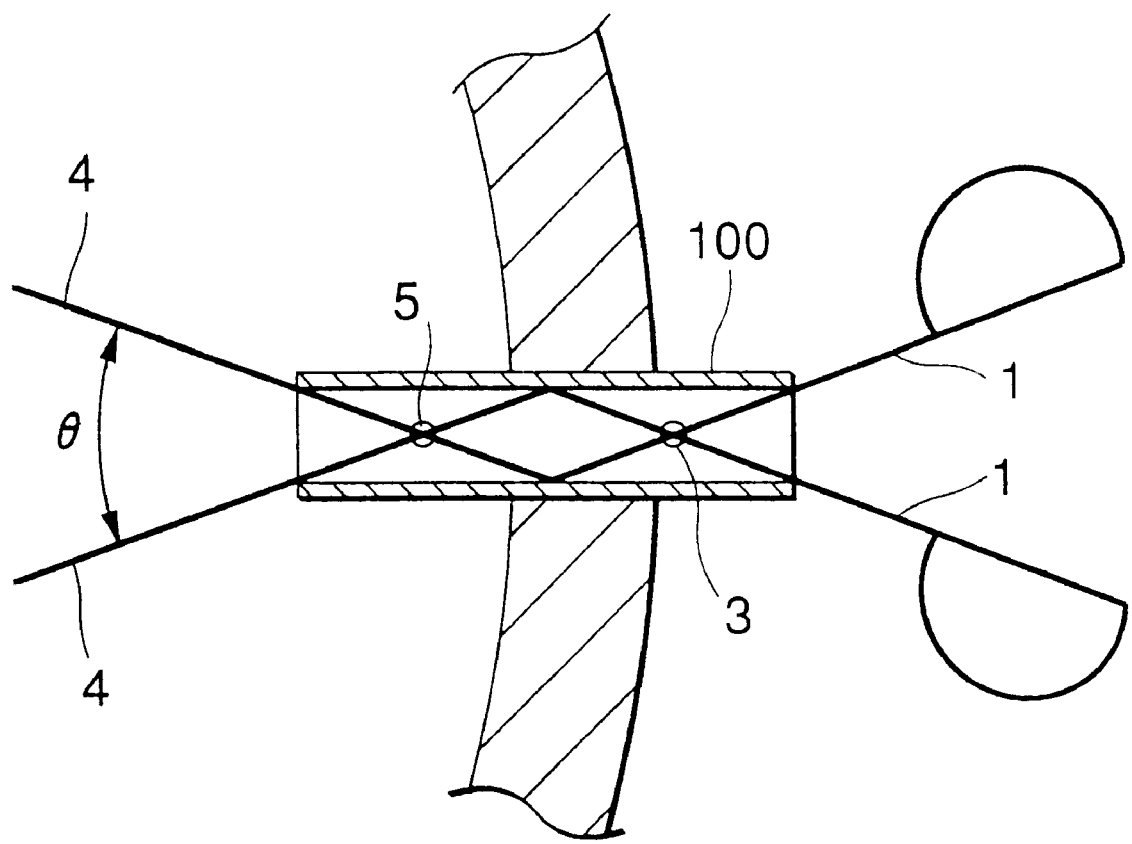
FIG. 3 is a diagram showing a use state of the first forceps.

FIG. 3 schematically shows a state where the first forceps for an endoscopic operation is used with being passed through the trocar 100. The open angle θ of the tip-end forceps pieces 4 is restricted by the inner diameter of the trocar 100, particularly, the width of the both end openings.

The first and second fulcrum 3 and 5 are located at positions which are closer to the both end openings than the middle of the trocar 100, respectively. Consequently, Tan(θ/2) can be made larger, so that the tip-end forceps pieces 4 can be widely opened.

In an endoscopic operation, therefore, even a large diseased part can be easily grasped or cut while passing the forceps through the usual trocar 100. When the distance between the first and second fulcrum 3 and 5 is set to be no less than the length of the trocar 100, the open angle θ is not restricted by the dimensions of the trocar 100.

Figure 4:
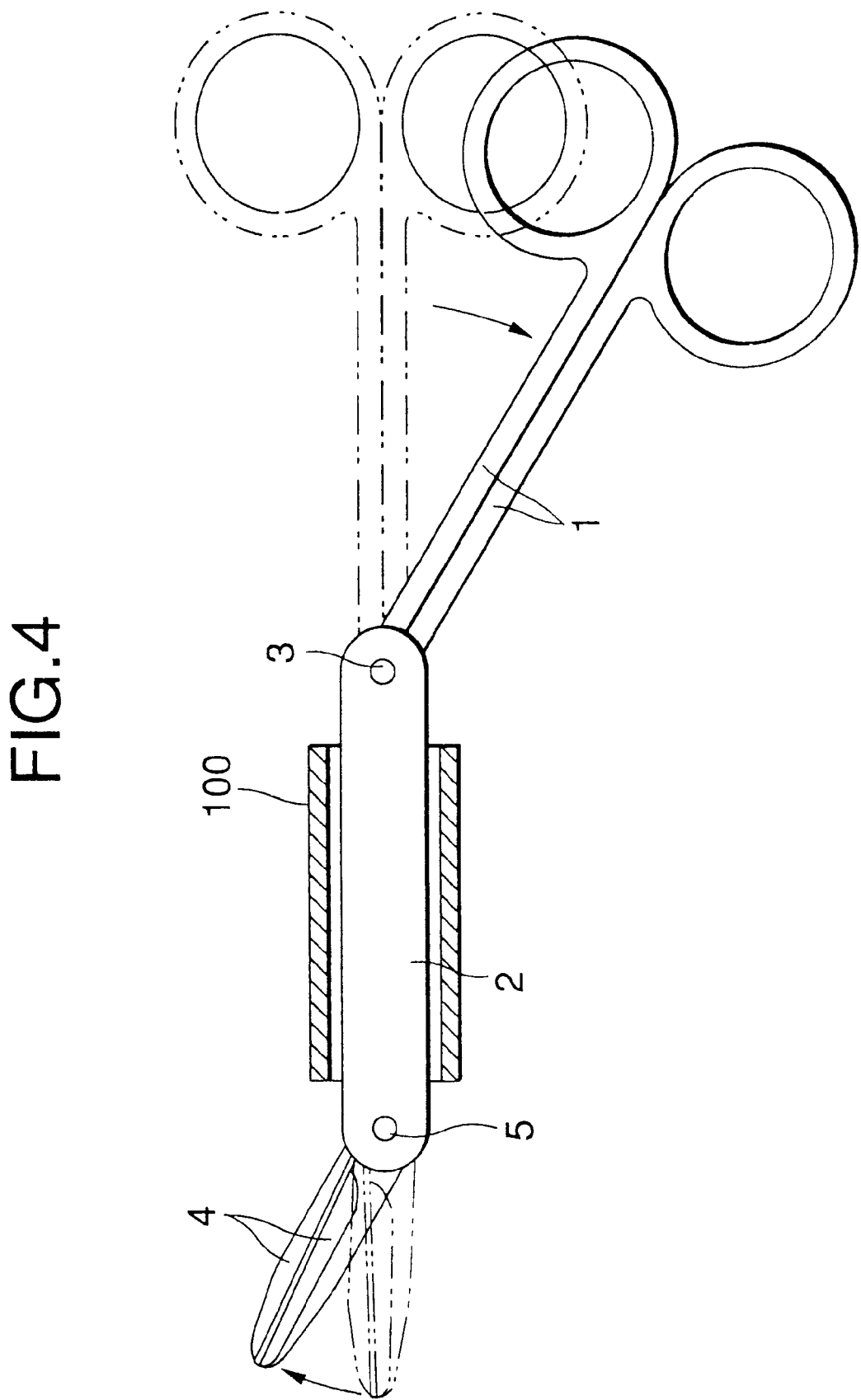
FIG. 4 is a front view of the cutting forceps and illustrating the function of the first forceps.

As shown in FIG. 4, the pair of grip pieces 1 may be swung in the same direction about the first fulcrum 3. This causes the pair of tip-end forceps pieces 4 to be swung together about the second fulcrum 5. Consequently, operations such as grasping and cutting can be easily performed on even a diseased part which is not in front of the trocar 100.

Figure 5:
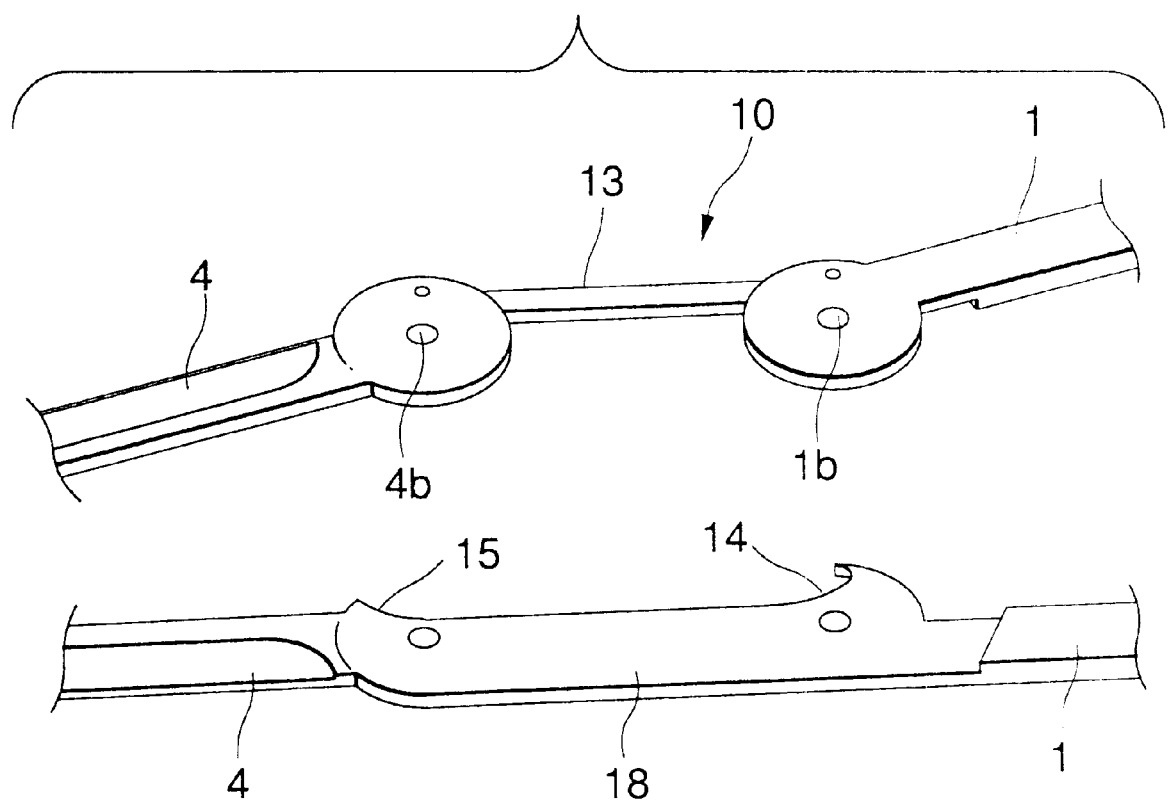
FIG. 5 is an exploded perspective view of an operation transferring unit of a second forceps for an endoscopic operation.

FIG. 5 shows a second forceps for an endoscopic operation. One of the grip pieces 1 and one of the tip-end forceps pieces 4 are coupled with each other by the arm 13 in the same manner as the first forceps, and the other grip piece and the other tip-end forceps piece are integrally formed via a coupling plate 18.

According to this configuration, although only one of the paired tip-end forceps pieces 4 is operated by the grip pieces 1, the opening and closing operations of the tip-end forceps pieces 4 can be realized by a simple structure of the operation transferring unit 10.

In this second forceps for an endoscopic operation, the swing range of the tip-end forceps pieces 4 is regulated by abutting the arm 13 on the recess 15 of the tip-end forceps pieces 4 side. Such a single-fixed structure may be employed also in forceps for an endoscopic operation described below.

Figure 6A:
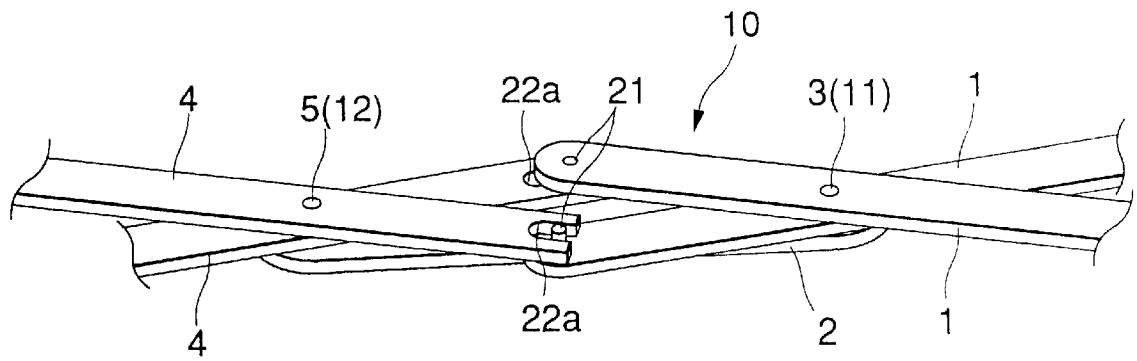
FIGS. 6A and 6B are exploded perspective views of an operation transferring unit of a third forceps for an endoscopic operation.
Figure 6B:
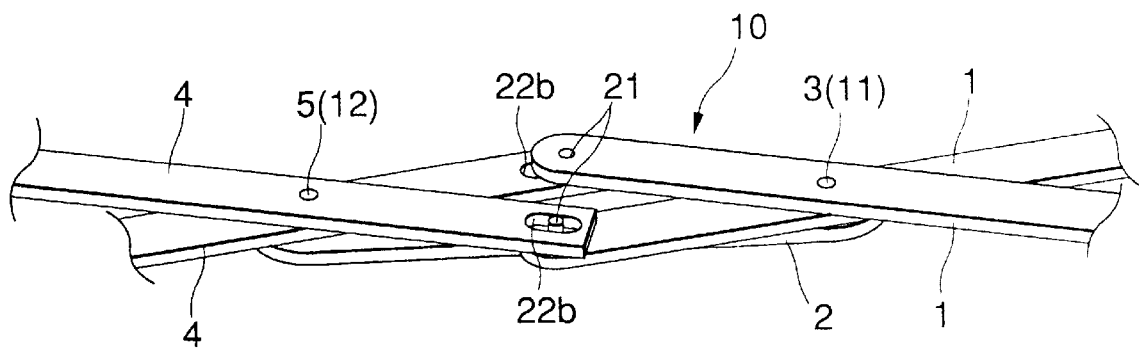

FIGS. 6A and 6B show a third forceps for an endoscopic operation. The operation transferring unit 10 is configured by pins 21 respectively projected from end portions of the grip pieces 1 which swing about the first fulcrum 3, and long grooves 22a or long holes 22b respectively formed in end portions of the tip-end forceps pieces 4 which swing about the second fulcrum 5.

The long grooves 22a or the long holes 22b are formed in the end portions of the tip-end forceps pieces 4 in the longitudinal direction of the tip-end forceps pieces 4. The pins 21 are formed so as to have a thickness at which the pins can be moved in the long grooves 22a or the long holes 22b without backlash and resistance.

When the grip pieces 1 are operated to be mutually opened or closed about the first fulcrum 3, therefore, the operation is transferred to the tip-end forceps pieces 4 via the pins 21 and the long grooves 22a or the long holes 22b, so that the tip-end forceps pieces 4 are mutually opened or closed.

Alternatively, the pins 21 may be disposed on the tip-end forceps pieces 4 and the long grooves 22a or the long holes 22b may be disposed in the grip pieces 1. As shown in FIG. 6B, the long holes 22b which close an outside ends of the tip-end forceps pieces 4 may be constructed so as to pass the pins 21. In this construction, the opening angle of the tip-end forceps pieces 4 is regulated by abutting the pin 21 on an outside ends of the long holes 22b.

Figure 7:
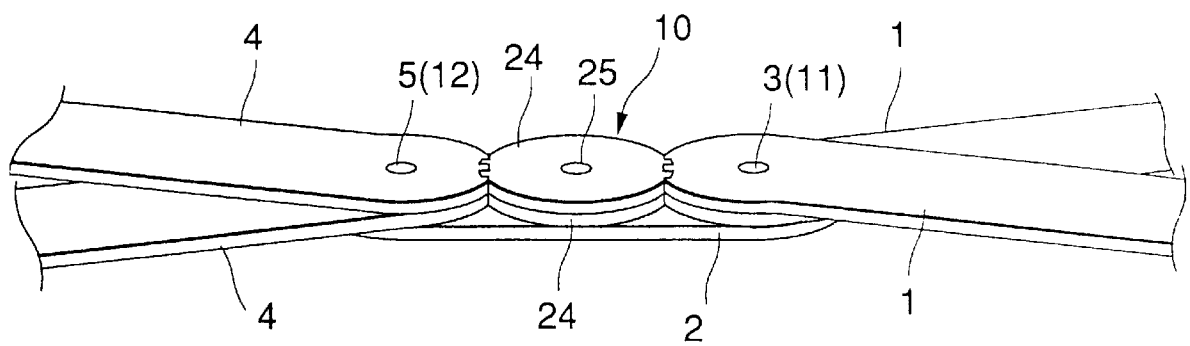
FIG. 7 is an exploded perspective view of an operation transferring unit of a fourth forceps for an endoscopic operation.

FIG. 7 shows a fourth forceps for an endoscopic operation. A gear 24 is supported on the support side plate 2 so as to be rotatable about a shaft 25. The gear 24 meshes with a member on the side of the grip pieces 1 which swing about the first fulcrum 3, and with a member on the side of the tip-end forceps pieces 4 which swing about the second fulcrum 5.

According to this configuration, when the grip pieces 1 are operated to be mutually opened or closed about the first fulcrum 3, the operation is transferred to the tip-end forceps pieces 4 via the gear 24, so that the tip-end forceps pieces 4 are mutually opened or closed.

Figure 8:
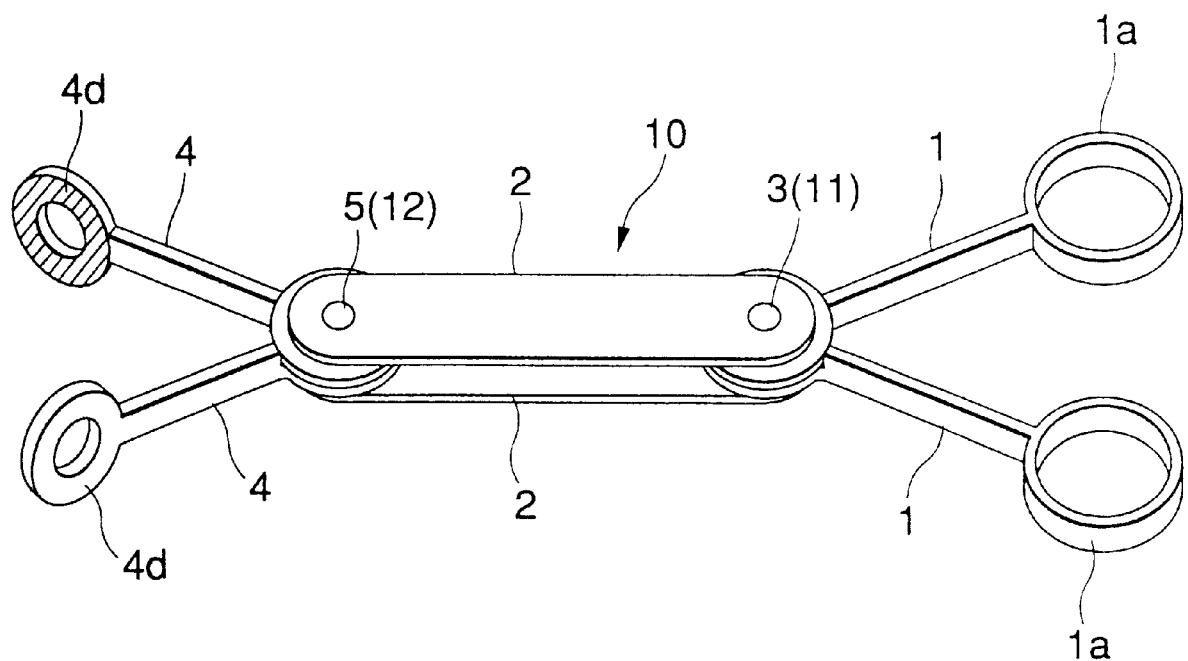
FIG. 8 is an exploded perspective view of an operation transferring unit of a fifth forceps for an endoscopic operation.

FIG. 8 shows a fifth forceps for an endoscopic operation which is applied to a grasping forceps. In the fifth forceps, doughnut-shaped holding portions 4d are formed at the front ends of the tip-end forceps pieces 4, respectively. The holding portions may have any other adequate shape. Any one of the operation transferring units of the above-described forceps may be used as the operation transferring unit 10 of this fifth forceps.

The foregoing description of the preferred embodiments of the invention has been presented for the purpose of illustration and description only. It is not intended to be exhaustive or to limit the invention to the precise form disclosed, and modifications and variations are possible in light of and within the scope of the invention. The preferred embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and equivalents thereof.

According to the above-described forceps, the grip pieces and the tip-end forceps pieces are respectively opened or closed about two fulcrums which are separated from each other. Therefore, the tip end forceps pieces can be widely opened under a state where the forceps is passed through a usual trocar, and even a large diseased part can be easily grasped or cut in an endoscopic operation.

What is claimed is:

1. A forceps for an endoscopic operation comprising:
   a pair of grip pieces, each of said grip pieces being pivotally supported to be movable towards and away from each other about a first fulcrum;
   a pair of tip-end forceps pieces, each of said tip-end pieces being pivotally supported to be movable towards and away from each other about a second fulcrum separated from said first fulcrum, the distance between said first fulcrum and said second fulcrum being constant during movement of said pair of grip pieces and said tip-end pieces;
   an operation transferring member which transfers movement of each of said pair of grip pieces about said first fulcrum to corresponding movement of each of said pair of tip-end forceps pieces about said second fulcrum; and
   a line connecting said first fulcrum and said second fulcrum, wherein both of said pair of tip-end forceps pieces also move in the same direction about said second fulcrum to one side of said line when both of said pair of grip pieces are moved in the same direction about said first fulcrum to the other side of said line.

2. A forceps for an endoscopic operation according to claim 1, wherein said operation transferring member has a thickness which passes through a trocar.

3. A forceps for an endoscopic operation according to claim 1, wherein said operation transferring member comprises an arm which is link-coupled to a first member provided on a first fulcrum side of said grip pieces, and to a second member provided on a second fulcrum side of said tip-end forceps pieces.

4. A forceps for an endoscopic operation according to claim 1, wherein said operation transferring member comprises:
   a pin projected from one of a third member provided on a first fulcrum side of said grip pieces, and a fourth member provided on a second fulcrum side of said tip-end forceps pieces; and
   a long groove which engages with said pin and is formed in the other of said third member and said fourth member.

5. A forceps for an endoscopic operation according to claim 1, wherein said operation transferring member comprises a gear which meshes with a fifth member provided on a first fulcrum side of said grip pieces, and with a sixth member provided on a second fulcrum side of said tip-end forceps pieces.

6. A forceps for an endoscopic operation according to claim 1, wherein said operation transferring member abuts a portion of at least one of said grip pieces and said tip-end forceps pieces to regulate a swing range of said tip-end forceps.

7. A forceps for an endoscopic operation according to claim 1, wherein said tip-end forceps pieces are scissors members.

8. A forceps for an endoscopic operation according to claim 1, wherein said tip-end forceps pieces are grasping members.

* * * * *